(12) United States Patent
Tashiro

(10) Patent No.: US 10,561,299 B2
(45) Date of Patent: Feb. 18, 2020

(54) MEDICAL INFORMATION RECORDING DEVICE

(71) Applicant: OLYMPUS CORPORATION, Hachioji-shi, Tokyo (JP)

(72) Inventor: Junichi Tashiro, Higashimurayama (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/949,215

(22) Filed: Apr. 10, 2018

(65) Prior Publication Data
US 2018/0220872 A1   Aug. 9, 2018

Related U.S. Application Data

(63) Continuation of application No. PCT/JP2016/077816, filed on Sep. 21, 2016.

(30) Foreign Application Priority Data

Oct. 19, 2015   (JP) ................................ 2015-205710

(51) Int. Cl.
*A61B 1/045*   (2006.01)
*H04N 21/41*   (2011.01)
(Continued)

(52) U.S. Cl.
CPC .......... *A61B 1/0002* (2013.01); *A61B 1/0005* (2013.01); *A61B 1/00006* (2013.01);
(Continued)

(58) Field of Classification Search
CPC .............. A61B 1/0002; A61B 1/00006; A61B 1/00009; A61B 1/00045; A61B 1/0005;
(Continued)

(56) References Cited

U.S. PATENT DOCUMENTS

2005/0070783 A1* 3/2005 Yanagita ................... A61B 6/00
                                                                          600/407
2006/0255535 A1* 11/2006 Takano ...................... B65H 5/34
                                                                          271/270

(Continued)

FOREIGN PATENT DOCUMENTS

CN            104684452 A     6/2015
EP              2881030 A1    6/2015
(Continued)

OTHER PUBLICATIONS

Dec. 20, 2016 International Search Report issued in Patent Application No. PCT/JP2016/077816.

*Primary Examiner* — Thai Q Tran
*Assistant Examiner* — Jose M Mesa
(74) *Attorney, Agent, or Firm* — Oliff PLC

(57) ABSTRACT

A medical information recording device includes a first recording processing unit configured to record a moving image of a medical image in which a status information image is superimposed, a second recording processing unit configured to record a moving image of the medical image in which a portion of the status information image of the medical image is subjected to mask processing, an arbitration unit configured to control communication between a recording unit in which the medical image in which the status information image is superimposed and the medical image in which the portion of the status information image is subjected to mask processing are recorded, and the first recording processing unit and the second recording processing unit, and a load adjusting circuit configured to control the arbitration unit on the basis of load of the first recording processing unit and the second recording processing unit.

14 Claims, 11 Drawing Sheets

(51) Int. Cl.
*G06T 11/60* (2006.01)
*A61B 1/00* (2006.01)
*H04N 21/81* (2011.01)
*H04N 21/431* (2011.01)
*H04N 21/44* (2011.01)
*H04N 21/433* (2011.01)

(52) U.S. Cl.
CPC ...... *A61B 1/00009* (2013.01); *A61B 1/00045* (2013.01); *A61B 1/045* (2013.01); *G06T 11/60* (2013.01); *H04N 21/41* (2013.01); *H04N 21/4318* (2013.01); *H04N 21/4334* (2013.01); *H04N 21/44008* (2013.01); *H04N 21/816* (2013.01)

(58) Field of Classification Search
CPC .... G06T 11/60; H04N 21/41; H04N 21/4318; H04N 21/4334; H04N 21/44008; H04N 21/816
See application file for complete search history.

(56) References Cited

U.S. PATENT DOCUMENTS

| | | | |
|---|---|---|---|
| 2011/0206282 A1* | 8/2011 | Aisaka | G06T 11/60 382/195 |
| 2013/0182184 A1* | 7/2013 | Senlet | H04N 5/272 348/586 |
| 2013/0202272 A1* | 8/2013 | Minoshima | H04N 5/772 386/278 |
| 2014/0375768 A1 | 12/2014 | Tsuchiya et al. | |
| 2014/0379382 A1* | 12/2014 | Morishima | G06F 19/321 705/3 |

FOREIGN PATENT DOCUMENTS

| | | |
|---|---|---|
| JP | 2007-319342 A | 12/2007 |
| JP | 5690450 B2 | 3/2015 |
| WO | 2014/103879 A1 | 7/2014 |

* cited by examiner

FIG. 3

| No | DISPLAY MODE | PATTERN | REGION IN MEDICAL IMAGE |
|---|---|---|---|
| 1 | 5:4 | A | R1 |
| 2 | 4:3 | B | R2 |
| 3 | 16:9 | C | R3 |
| 4 | 16:10 | D | R4 |
| ⋮ | ⋮ | ⋮ | ⋮ |

MEDICAL INFORMATION RECORDING DEVICE

CROSS REFERENCE TO RELATED APPLICATION

This application is a continuation application of PCT/JP2016/077816 filed on Sep. 21, 2016 and claims benefit of Japanese Application No. 2015-205710 filed in Japan on Oct. 19, 2015, the entire contents of which are incorporated herein by this reference.

BACKGROUND OF THE INVENTION

1. Field of the Invention

The present invention relates to a medical information recording device which records an image obtained by a medical device such as an endoscope.

2. Description of the Related Art

In recent years, an endoscope has been widely employed in a medical field, or the like. A medical image obtained by the endoscope is recorded in various kinds of media to record diagnosis and a case. Further, in accordance with increase in capacity of a recording medium, a movie from the endoscope has been also recorded. Such recording processing of a medical image is digitally performed, and there is a case where the medical image is stored in a computer readable file format.

In a conventional medical information recording device which records a medical image, recorded data can be outputted in various formats in accordance with application. For example, the medical image can be also recorded in a semiconductor recording device such as a USB memory, and data can be shared by transferring the data to a server via a network and recording the data.

By the way, in the case where a medical image such as an endoscope image and an ultrasound image is recorded for the purpose of diagnosis, or the like, it would be better to record information regarding a patient who is a target of the medical image along with the medical image. For example, a character image (hereinafter, referred to as a patient information image) such as patient name and a patient ID included in patient information is superimposed on the medical image so as to make it clear a patient for the recorded medical image.

There is a case where such a medical image is recorded for backup for an evidence image, or the like, or as an educational material. For example, concerning an important anatomy scene in a case, it is possible to share the recorded image at an academic conference or a nosocomial conference to be utilized for education of young doctors.

By the way, when a case image is presented at an academic conference, in terms of confidentiality, it is necessary to reproduce a moving image from which a patient information image is deleted. In normal operation, a medical image is rarely recorded assuming secondary use of the recorded medical image at an academic conference, and a medical image to be secondarily used is selected for presentation at an academic conference. Therefore, a patient information image is typically recorded by being superimposed on a medical image upon recording of the medical image, and it is necessary to perform editing processing of deleting the patient information image upon presentation at the academic conference (upon secondary use).

However, to delete an image of a specific portion in a moving image, it is necessary to perform mask processing of superimposing another image on the specific portion, mosaic processing of applying mosaic at the specific portion, or the like. These kinds of processing for deleting the specific portion (hereinafter, referred to as mask processing) requires extremely troublesome work such as editing and processing work using, for example, a video editing software.

Note that Japanese Patent Application Laid-Open Publication No. 2007-319342 discloses a device for obtaining an image in which a patient information image is subjected to mask processing.

SUMMARY OF THE INVENTION

A medical information recording device according to one aspect of the present invention includes a first recording processing unit configured to record a moving image of a medical image in which a status information image is superimposed, a second recording processing unit configured to record a moving image of a medical image in which a portion of the status information image in the medical image is subjected to mask processing, an arbitration unit configured to control communication between a recording unit in which the medical image in which the status information image is superimposed and the medical image in which the portion of the status information image is subjected to mask processing are recorded, and the first recording processing unit and the second recording processing unit, and a load adjusting circuit configured to control the arbitration unit on the basis of load of the first recording processing unit and the second recording processing unit.

BRIEF DESCRIPTION OF THE DRAWINGS

FIG. 3 is an explanatory diagram for explaining content of an information table stored in a memory 40 in FIG. 1;

DETAILED DESCRIPTION OF THE PREFERRED EMBODIMENTS

Embodiments of the present invention will be described in detail below with reference to the drawings.

First Embodiment

Figure 1:
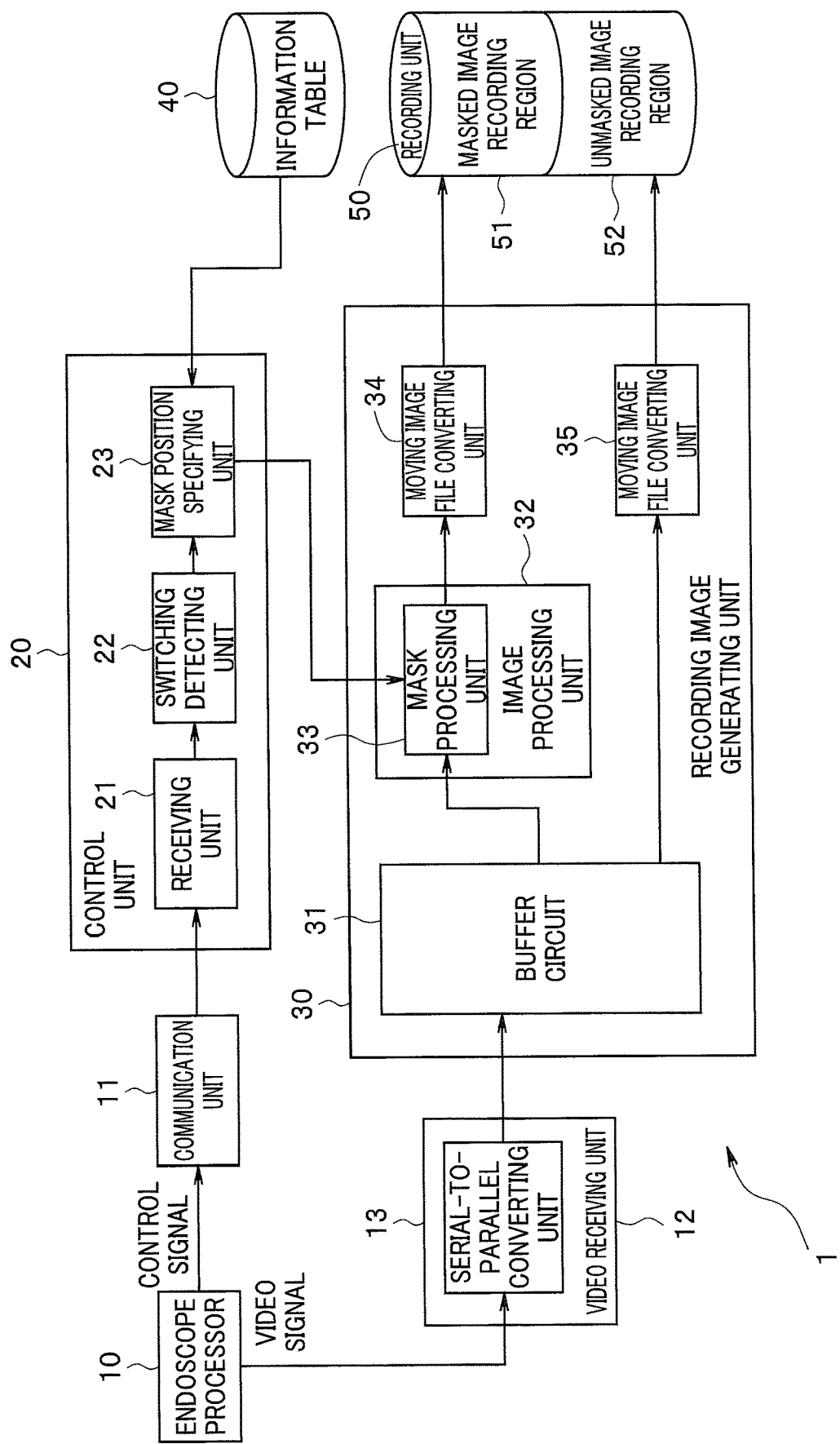
FIG. 1 is a block diagram illustrating a medical information recording system into which a medical information recording device is incorporated according to a first embodiment of the present invention.
Figure 2A:
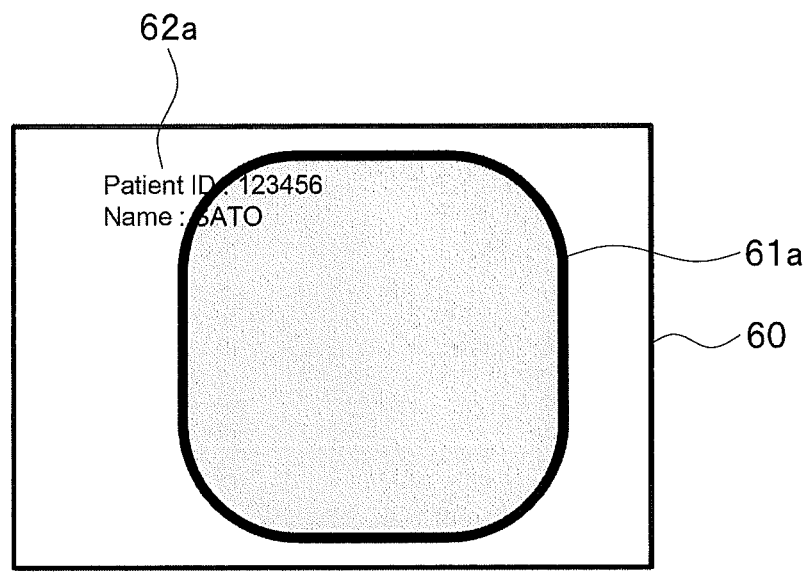
FIG. 2A is an explanatory diagram illustrating a medical image in a display mode of 5:4.
Figure 2B:
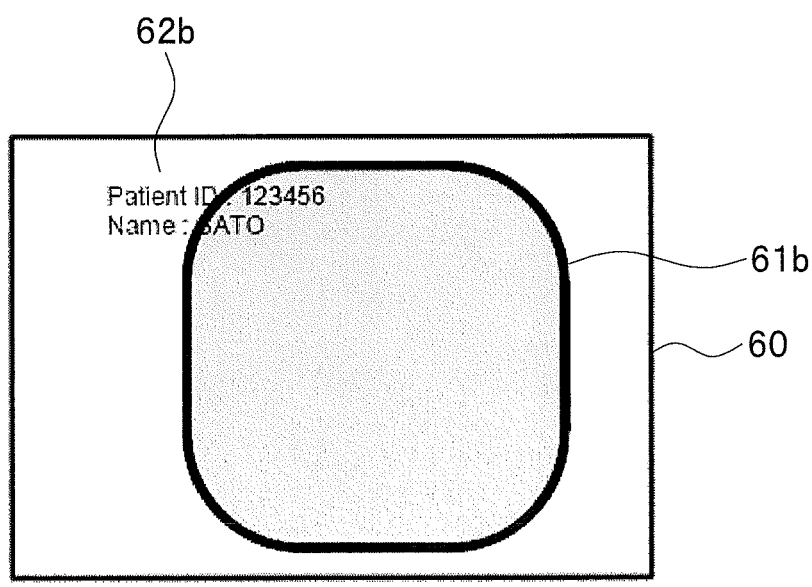
FIG. 2B is an explanatory diagram illustrating a medical image in a display mode of 4:3.
Figure 2C:
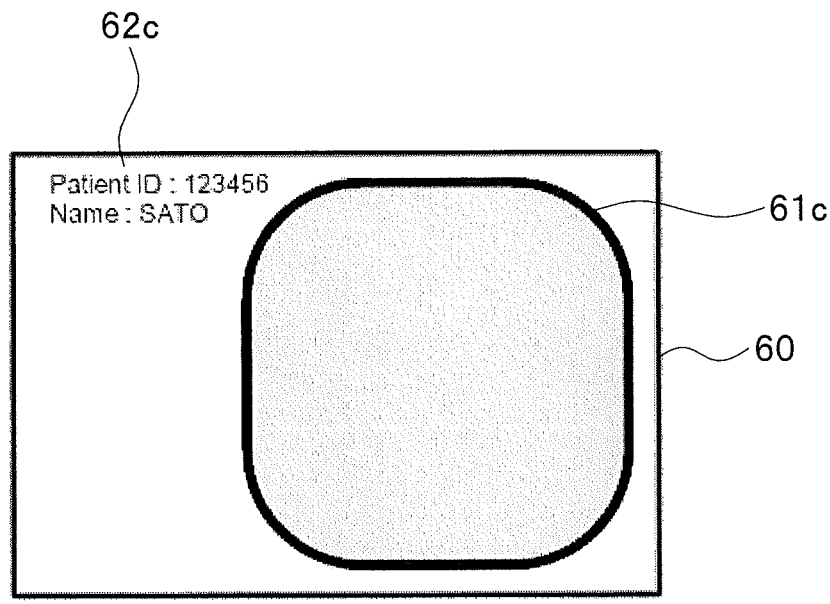
FIG. 2C is an explanatory diagram illustrating a medical image in a display mode of 16:9.
Figure 2D:
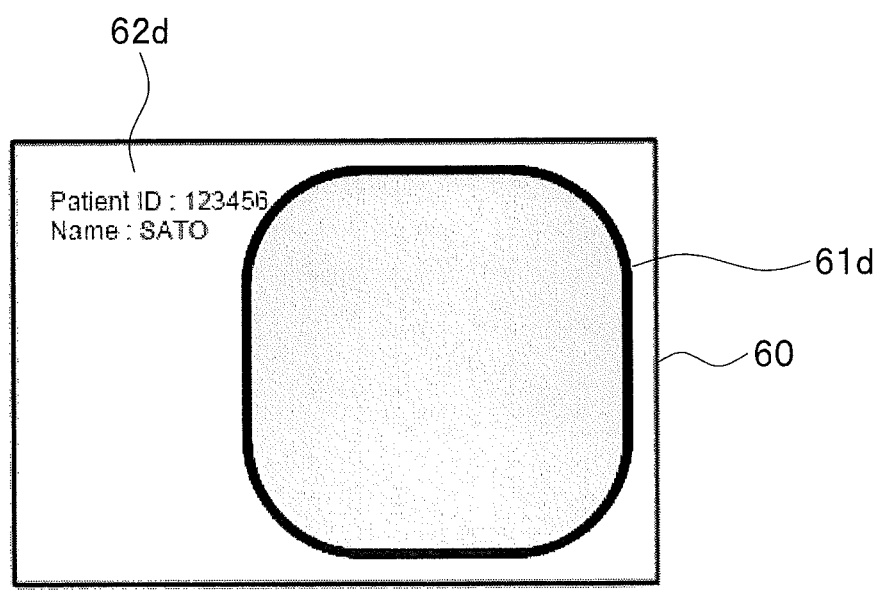
FIG. 2D is an explanatory diagram illustrating a medical image in a display mode of 16:10.

FIG. 1 is a block diagram illustrating a medical information recording system into which a medical information recording device is incorporated according to a first embodiment of the present invention.

In the present embodiment, an example will be described where an endoscope processor 10 is used as a device which outputs medical information. The endoscope processor 10 can capture an image from an endoscope, or the like, which is not illustrated, can perform image signal processing and can generate a medical image such as an endoscope image.

The endoscope processor 10 can, for example, capture patient information which is information regarding a patient, such as name and a patient ID of a patient, and examination information, via an input device which is not illustrated, and can superimpose an image based on the patient information, for example, a character image of the name or the patient ID of the patient on the medical image generated on the basis of output of the endoscope, or the like, as a patient information image. The endoscope processor 10 outputs the medical image in which the patient information image is superimposed to a video receiving unit 12 configuring the medical information recording device 1.

Note that it is also possible to superimpose a status information image regarding status information indicating various kinds of statuses, as well as the patient information, on the endoscope image. In the following description, while the patient information and the patient information image will be described, the following description can similarly apply to the status information and the status information image.

The endoscope processor 10 can output a medical image in a plurality of display modes. The endoscope processor 10 can output an image obtained by converting an endoscope image to an image supporting a display mode such as 5:4, 4:3, 16:9 and 16:10 in accordance with a size, or the like, of a display screen of a monitor even if an aspect ratio of the endoscope image is, for example, 16:9.

Further, the endoscope processor 10 can generate and output a control signal including information on the display mode. The control signal from the endoscope processor 10 is provided to the communication unit 11. The communication unit 11 outputs the received control signal to the control unit 20 configuring the medical information recording device 1.

FIG. 2A to FIG. 2D are explanatory diagrams illustrating a medical image in each display mode. FIG. 2A to FIG. 2D respectively illustrate display modes of 5:4, 4:3, 16:9 and 16:10. In FIG. 2A to FIG. 2D, endoscope images 61a to 61d are included in each medical image 60. These endoscope images 61a to 61d are based on a common endoscope image, and are disposed at positions different from one another in the medical image 60 in accordance with the display mode. In a similar manner, in FIG. 2A to FIG. 2D, patient information images 62a to 62d based on the patient information are included in the medical image 60. These patient information images 62a to 62d are disposed at positions different from one another in the medical image 60 in accordance with the display mode.

The positions of the patient information images 62a to 62d in the medical image 60 depend on the display mode, and if the display mode is known, it is obvious which region in the medical image 60 is allocated to the patient information images 62a to 62d. Note that patterns of positional relationship between the endoscope image and the patient information image on the medical image in the display modes of 5:4, 4:3, 16:9 and 16:10 are respectively set as patterns A to D.

In the present embodiment, in the medical information recording device 1, information indicating a region of the patient information image on the medical image is stored in a memory 40 as an information table.

FIG. 3 is an explanatory diagram for explaining content of the information table stored in the memory 40. In the example of FIG. 3, in regions No. 1 to 4 of the information table, information regarding the display modes of 5:4, 4:3, 16:9 and 16:10 are respectively recorded. FIG. 3 indicates that, in the display modes of 5:4, 4:3, 16:9 and 16:10, patterns of the positional relationship between the endoscope image and the patient information image on the medical image are respectively patterns A to D, and regions of the patient information images on the medical image (hereinafter, referred to as patient information image regions) are respectively regions R1 to R4.

The receiving unit 21 of the control unit 20 receives a control signal from the communication unit 11 and outputs the received control signal to a switching detecting unit 22. The switching detecting unit 22 detects whether or not the display mode is changed from the control signal and, if the display mode is changed, outputs the changed display mode to a mask position specifying unit 23. If the display mode is provided from the switching detecting unit 22, the mask position specifying unit 23 as a region judging unit specifies which of the regions R1 to R4 a current display mode corresponds to by referring to the memory 40 using the display mode, and outputs information on the specified patient information image region to a mask processing unit 33.

The video receiving unit 12 receives a video signal from the endoscope processor 10 and outputs the video signal to a recording image generating unit 30. For example, the video receiving unit 12, which includes a serial-to-parallel converting unit 13, converts a serial video signal into a parallel signal and provides the parallel signal to the recording image generating unit 30.

A buffer circuit 31 of the recording image generating unit 30, in which the video signal from the serial-to-parallel converting unit 13 is stored, outputs the stored video signal after dividing the video signal into two systems. One video signal outputted from the buffer circuit 31 is provided to a moving image file converting unit 35. The moving image file converting unit 35 as a first recording processing unit converts the inputted video signal into a moving image file and outputs the moving image file to a recording unit 50. That is, the moving image file converting unit 35 converts a medical image on which a patient information image remains superimposed into a moving image file and records the moving image file.

The recording unit 50 has two recording regions of a masked image recording region 51 and an unmasked image recording region 52, and records the moving image file from the moving image file converting unit 35 in the unmasked image recording region 52.

The other video signal outputted from the buffer circuit 31 is provided to an image processing unit 32. The image processing unit 32 includes a mask processing unit 33. The mask processing unit 33 receives the information on the patient information image region from the mask position specifying unit 23 and performs mask processing of converting the patient information image region in the medical image into a masked image. The mask processing unit 33 can convert the patient information image into the masked image through, for example, filling processing of filling a designated region with black, or the like. Further, the mask processing unit 33 can convert the patient information image into the masked image by, for example, performing mosaic processing on the designated patient information image region.

The image processing unit 32 outputs the video signal of the medical image in which the patient information image is masked (hereinafter, also referred to as a masked image) to the moving image file converting unit 34. The moving image file converting unit 34 as a second recording processing unit converts the inputted video signal into a moving image file, provides the moving image file to the recording unit 50 and causes the recording unit 50 to record the moving image file. The recording unit 50 records the masked image from the moving image file converting unit 34 in the masked image recording region 51.

That is, in the present embodiment, the recording image generating unit 30 divides the medical image into two systems by the buffer circuit 31, obtains a masked image in which the patient information image is masked by performing mask processing on one medical image, and obtains a medical image in a state where the patient information image is superimposed without performing mask processing on the other medical image (hereinafter, also referred to as an unmasked image). In this manner, in the present embodiment, two types of medical images, that is, a masked image and an unmasked image are generated at the same time.

Note that examples of the control signal from the endoscope processor 10 can include a recording start signal which gives an instruction of starting recording of the medical image which is a movie, a recording termination signal which gives an instruction of terminating the recording, a still image recording signal which gives an instruction of recording a medical image which is a still image, an examination termination signal which gives an instruction of terminating an examination, or the like. For example, in the endoscope processor 10, image processing is controlled in response to various kinds of scope operation of a release button, a recording start button, or the like, provided at the endoscope, and a control signal in accordance with various kinds of scope operation can be generated and outputted to the control unit 20 of the medical information recording device 1. The control unit 20 may control mask processing on the basis of the control signal and control start, termination, or the like, of recording on the basis of the control signal.

Note that, while a case has been described where the recording image generating unit 30 always generates and records medical images of both a masked image and an unmasked image by input of the video signal from the endoscope processor 10, the recording image generating unit 30 may be configured such that whether or not to generate a masked image can be controlled in accordance with, for example, user operation.

Figure 4:
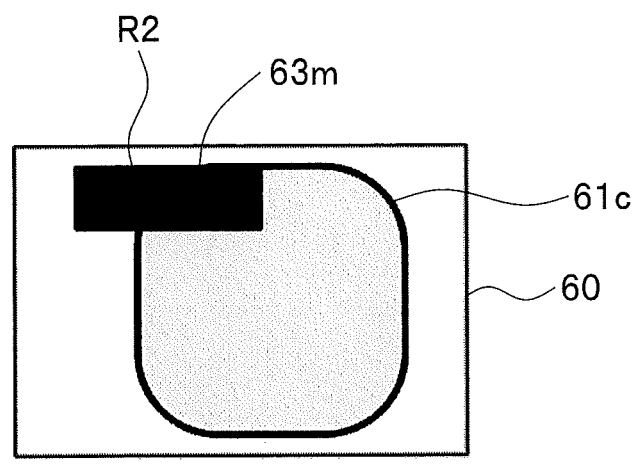
FIG. 4 is an explanatory diagram illustrating an example of a masked image.
Figure 5:
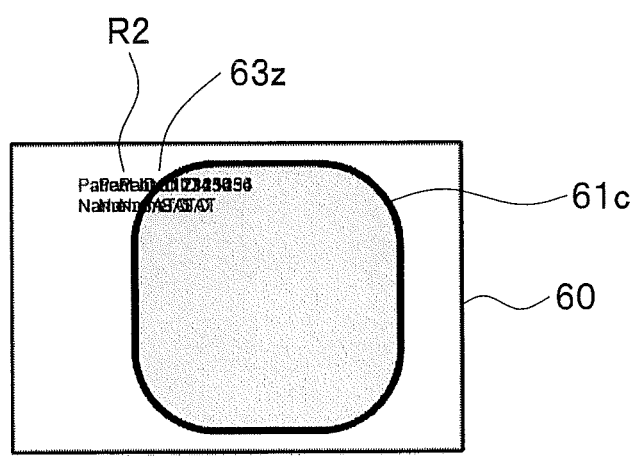
FIG. 5 is an explanatory diagram illustrating an example of the masked image.

Operation of the embodiment configured in this manner will be described next with reference to FIG. 4 and FIG. 5. FIG. 4 and FIG. 5 are explanatory diagrams illustrating an example of the masked image.

The endoscope image from the endoscope processor 10 is supplied to the recording image generating unit 30 via the video receiving unit 12. Further, the endoscope processor 10 outputs a control signal including information on the display mode of the video signal to be outputted to the control unit 20 via the communication unit 11. The receiving unit 21 of the control unit 20 receives the control signal and outputs the control signal to the switching detecting unit 22.

The switching detecting unit 22 outputs the information on the display mode to the mask position specifying unit 23 every time switching of the display mode is detected. The mask position specifying unit 23 acquires the information on the patient information image region for the display mode by referring to the information table stored in the memory 40 using the information on the display mode and outputs the acquired information to the mask processing unit 33 of the image processing unit 32.

The video signal inputted to the recording image generating unit 30 is provided to the buffer circuit 31. The buffer circuit 31 holds the inputted endoscope image (medical image) and divides the endoscope image into two systems. That is, one video signal from the buffer circuit 31 is provided to the moving image file converting unit 35 and converted into a moving image file. Further, the other video signal from the buffer circuit 31 is provided to the mask processing unit 33 of the image processing unit 32.

The mask processing unit 33 performs mask processing on the patient information image region of the inputted medical image. For example, the mask processing unit 33 fills the patient information image region with black. For example, it is assumed that the display mode of the video signal outputted from the endoscope processor 10 is 4:3. In this case, the mask position specifying unit 23 specifies that the patient information image region is the region R2 by referring to the information table in FIG. 3. The mask processing unit 33 superimposes a black image on a portion of the region R2 in the medical image.

FIG. 4 illustrates an example of the medical image in which the patient information image region is filled with black by the mask processing unit 33. FIG. 4 illustrates the medical image 60, the display mode of which is 4:3, and the endoscope image 61c is included in the medical image 60. Further, a portion corresponding to the region R2 on the medical image 60 is filled with a black image 63m.

In the medical image, the display mode of which is 4:3, the patient information image is superimposed on the portion of the region R2, and the patient information image is deleted by the masked image of the black image 63m.

Further, FIG. 5 illustrates an example of the medical image in which the patient information image region is subjected to mosaic processing by the mask processing unit 33. FIG. 5 illustrates the medical image 60, the display mode of which is 4:3, and the endoscope image 61c is included in the medical image 60. Further, a portion corresponding to the region R2 on the medical image 60 is converted into a masked image 63z by the mosaic processing.

In the medical image, the display mode of which is 4:3, the patient information image is superimposed on the portion of the region R2, and the patient information image is put into an invisible state by the masked image 63z by the mosaic processing.

The masked image from the mask processing unit 33 is provided to the moving image file converting unit 34 and converted into a moving image file. A moving image file of an unmasked image which is not subjected to mask processing, from the moving image file converting unit 35 is provided to the recording unit 50 and recorded in the unmasked image recording region 52. Further, the moving image file which is the masked image is provided to the recording unit 50 and recorded in the masked image recording region 51.

In this manner, in the present embodiment, the medical image in which the patient information image is superimposed is divided into two systems, and one medical image is converted into a moving image file as is at the recording image generating unit, while the other medical image is converted into a moving image file after the patient information image region is converted into the masked image by the mask processing unit. In this manner, the medical image including the patient information image and the medical image in which the patient information image is masked, that is, the patient information image is deleted are generated at the same time and recorded in the recording unit at the same time. Further, because the patient information image region is specified on the basis of the control signal including the information on the display mode and is automatically subjected to mask processing, it is possible to automatically and efficiently generate a medical image including a patient information image and a medical image which does not include a patient information image without a user performing troublesome work and without the user consciously deleting the patient information image. For example, it is possible to perform mask processing which automatically follows switching of the display mode of the endoscope image, so that it is not necessary to perform troublesome work such as changing of the mask position even in the case where the position of the patient information image superimposed in the image changes as a result of change of the display mode.

Further, because the mask position is specified by utilizing the display mode every time the display mode is switched, and it is not necessary to perform processing of specifying the mask position for each frame, it is possible to reduce processing required to specify the mask position.

Second Embodiment

Figure 6:
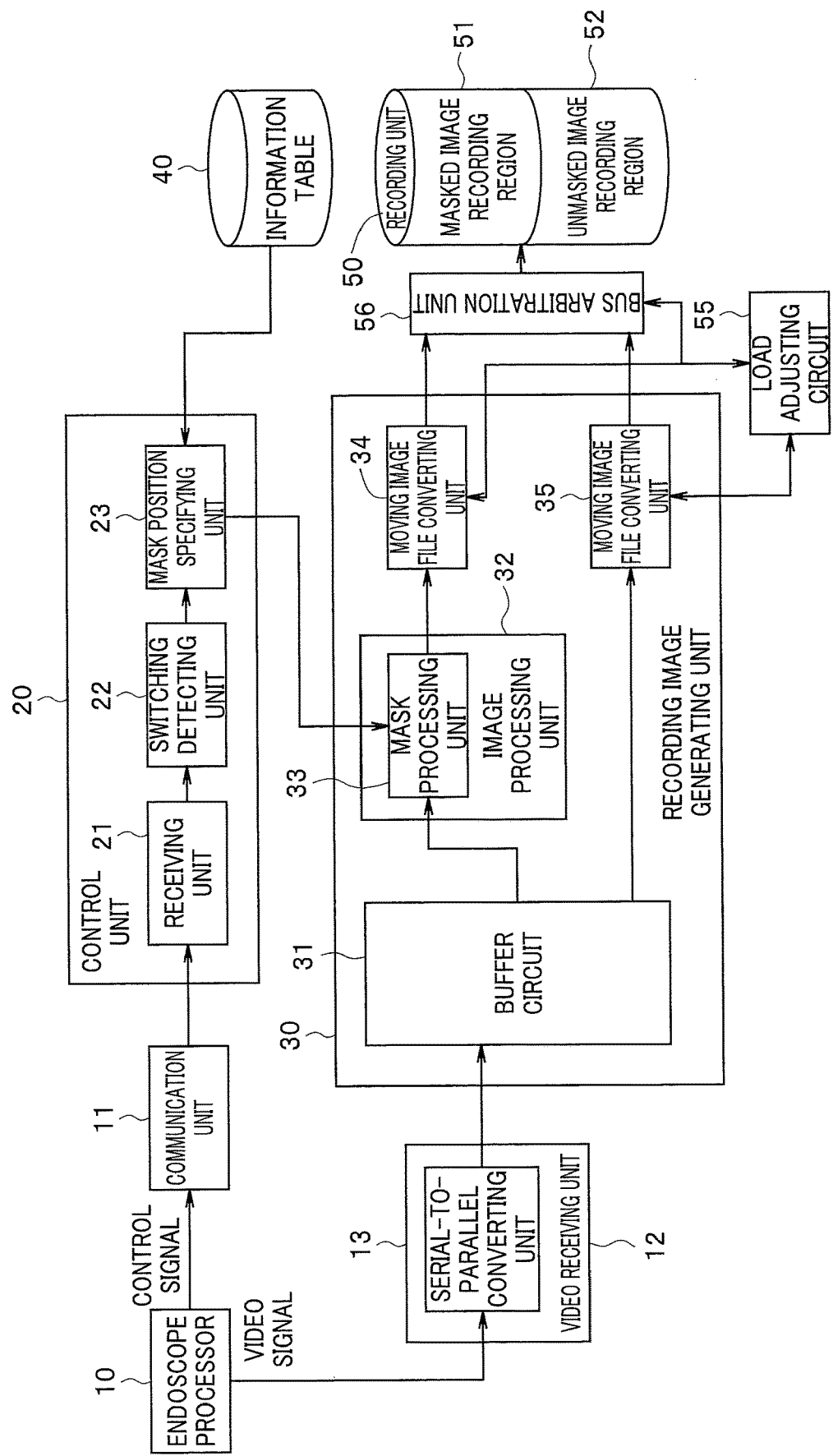
FIG. 6 is a block diagram illustrating a second embodiment of the present invention.

FIG. 6 is a block diagram illustrating a second embodiment of the present invention. In FIG. 6, the same reference numerals are assigned to components which are the same as the components in FIG. 1, and description will be omitted.

In the first embodiment, in order to record moving image files of both the masked image and the unmasked image at the same time, the recording image generating unit 30 and the recording unit 50 are connected via two systems of communication paths. In contrast, in the present embodiment, the recording image generating unit 30 and the recording unit 50 are connected via one system of a communication path.

The present embodiment is different from the first embodiment in that a load adjusting circuit 55 and a bus arbitration unit 56 are added. The moving image file converting units 34, 35 provide the generated moving image files to the recording unit 50 via the bus arbitration unit 56. Information relating to data amounts of the moving image files outputted from the moving image file converting units 34, 35 are provided to the load adjusting circuit 55.

The bus arbitration unit 56 provides the moving image files from the moving image file converting units 34, 35 to the recording unit 50. In this case, the bus arbitration unit 56 arbitrates transmission of the moving image file from the moving image file converting unit 34 and transmission of the moving image file from the moving image file converting unit 35 by being controlled by the load adjusting circuit 55, and transmits the moving image files in a time-division manner.

The load adjusting circuit 55 controls arbitration of the bus arbitration unit 56 on the basis of data amounts of the moving image files outputted from the moving image file converting units 34, 35. By this means, the bus arbitration unit 56 can reliably record the moving image files from the moving image file converting units 34, 35 in the recording unit 50.

Note that the load adjusting circuit 55 may control the bus arbitration unit 56 so that an unmasked image from the moving image file converting unit 35 among the moving image files from the moving image file converting units 34, 35, is preferentially transmitted to the recording unit 50.

Also in the embodiment configured in this manner, the moving image file of the unmasked image which is a medical image in a state where the patient information image is superimposed is outputted by the moving image file converting unit 35, and the moving image file of the masked image which is a medical image in which the patient information image is deleted is outputted by the moving image file converting unit 34.

The information relating to the data amounts of the moving image files generated by the moving image file converting units 34, 35 is supplied to the load adjusting circuit 55. The load adjusting circuit 55 controls transmission of the moving image files generated by the moving image file converting units 34, 35 on the basis of the data amounts of the moving image files generated by the moving image file converting units 34, 35.

The moving image files from the moving image file converting units 34, 35 are supplied to the recording unit 50 via the bus arbitration unit 56. The bus arbitration unit 56 reliably and efficiently records the moving image files in the recording unit 50 by controlling transmission of the moving image files in accordance with the data amounts of the moving image files from the moving image file converting units 34, 35 by being controlled by the load adjusting circuit 55. Further, the bus arbitration unit 56 may record the moving image file from the moving image file converting unit 35 in preference to the moving image file from the moving image file converting unit 34, in the recording unit 50.

In this manner, in the present embodiment, by transmission of two types of medical images of a masked image and an unmasked image being arbitrated, it is possible to reliably and efficiently record the medical images in the recording unit. Further, in the case where the two types of medical images of a masked image and an unmasked image cannot be transmitted and recorded at the same time for some reasons, the bus arbitration unit is controlled so that the movie in a state where the patient information image is superimposed is preferentially recorded. By this means, it is possible to reliably record at least a medical image in which the patient information image is superimposed.

Third Embodiment

Figure 7:
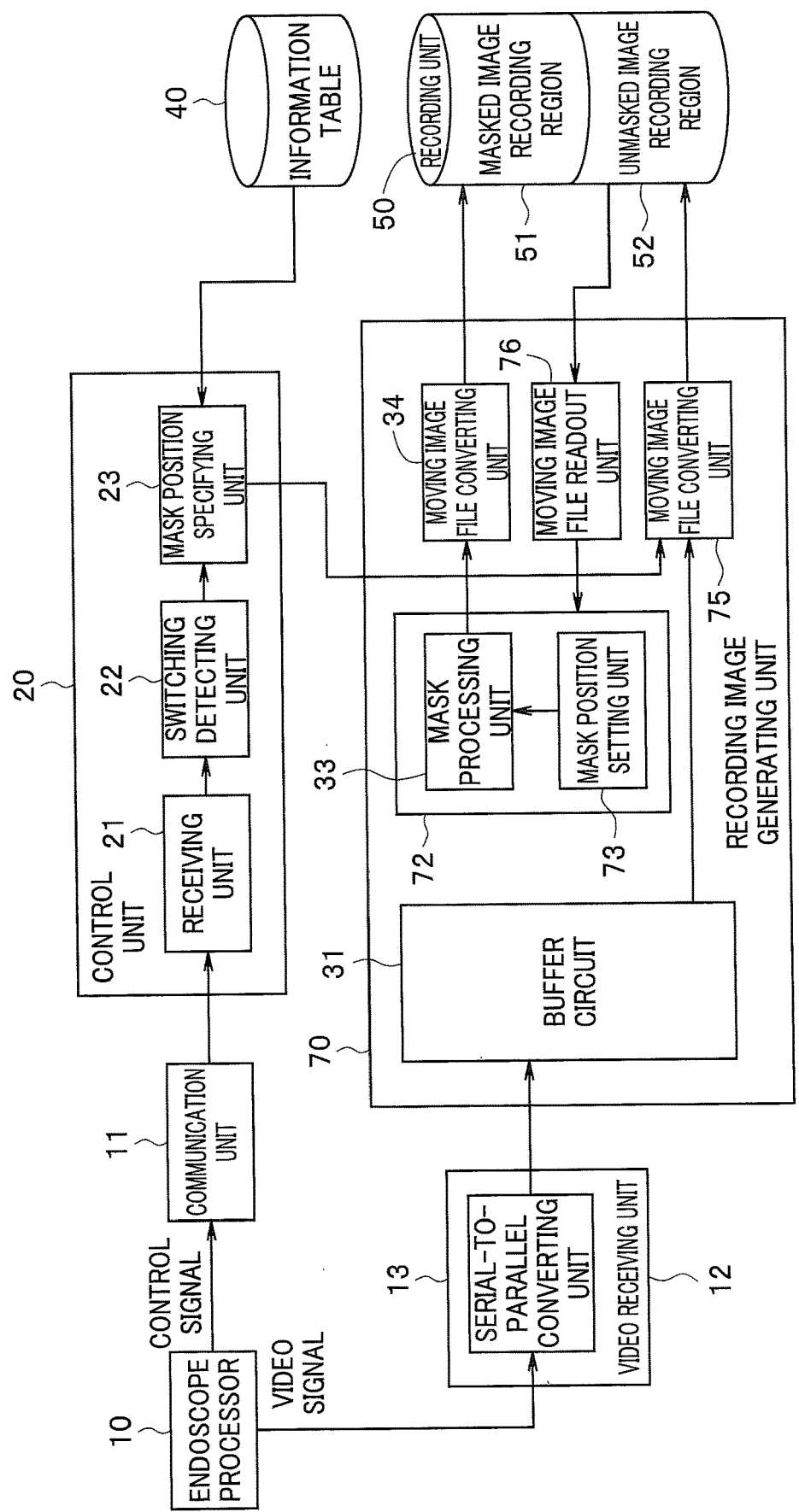
FIG. 7 is a block diagram illustrating a third embodiment of the present invention.

FIG. 7 is a block diagram illustrating a third embodiment of the present invention. In FIG. 7, the same reference numerals are assigned to components which are the same as the components in FIG. 1, and description will be omitted.

In the first embodiment, moving image files of both a masked image and an unmasked image are recorded at the same time. In contrast, in the present embodiment, an unmasked image which is a medical image in which the patient information image remains superimposed is recorded, and after this recording, the recorded unmasked image is read out to generate and record a masked image.

The present embodiment is different from the embodiment in FIG. 1 in that a recording image generating unit 70 is employed in place of the recording image generating unit 30. The recording image generating unit 70 is different from the recording image generating unit 30 in FIG. 1 in that an image processing unit 72 and a moving image file converting unit 75 are employed respectively in place of the image processing unit 32 and the moving image file converting unit 35, and a moving image file readout unit 76 is added.

The mask position specifying unit 23 of the control unit 20 outputs information on the patient information image region to the moving image file converting unit 75 instead of outputting to the image processing unit 32. The moving image file converting unit 75 converts the medical image in which the patient information image remains superimposed into a moving image file in a similar manner to the moving image file converting unit 35. Further, in the present embodiment, the moving image file converting unit 75 converts the information on the patient information image region from the mask position specifying unit 23 into metadata. The moving image file converting unit 75 records the generated moving image file and metadata in association with the unmasked image recording region 52 of the recording unit 50.

The moving image file readout unit 76 can read out the unmasked image and the metadata corresponding to the unmasked image recorded in the recording unit 50. The moving image file readout unit 76 outputs the read out unmasked image and metadata to the image processing unit 72.

The image processing unit 72 includes a mask processing unit 33 and a mask position setting unit 73. The mask position setting unit 73 can set the patient information image region at the mask processing unit 33 on the basis of the metadata from the moving image file readout unit 76. The mask processing unit 33 performs mask processing on the unmasked image read out by the moving image file readout unit 76. That is, the mask processing unit 33 performs mask processing of, for example, superimposing a black image on the patient information image region in the medical image. The mask processing unit 33 outputs the masked image which is the medical image after the mask processing to the moving image file converting unit 34.

Note that the recording image generating unit 70 can execute generation of the masked image at an arbitrary timing. For example, processing of generating and recording the masked image may be automatically executed when processing load of the whole circuit is low, or the processing may be executed at a predetermined timing defined in advance. In the case where an insertion portion of the endoscope is inserted into a body to observe body tissue, or the like, while change of the endoscope image is large when the insertion portion moves, change of the endoscope image is relatively small when the insertion portion is fixed. Therefore, in the case where the insertion portion is fixed, it can be considered that a data amount of the endoscope image is relatively small, and processing load at the recording image generating unit 70 is sufficiently low. Therefore, processing of generating and recording the masked image may be performed in such a case where the processing load is low. Accordingly, it is also possible to perform processing of generating and recording the masked image at the same time as recording of the unmasked image. Further, masking processing and recording processing may be performed in response to user operation. By this means, it is also possible to omit generation and recording of the masked image for the medical image for which the masked image is not required. Further, it is also possible to generate a masked image from the recorded unmasked image and record the masked image after an examination with the endoscope, or the like, is finished.

Operation of the embodiment configured in this manner will be described next. The operation is the same as the operation in the first embodiment in that the endoscope image from the endoscope processor 10 is supplied to the recording image generating unit 70 via the video receiving unit 12, and a control signal including information on the display mode from the endoscope processor 10 is supplied to the control unit 20 via the communication unit 11. Further, the operation is the same as the operation in the first embodiment also in that the mask position specifying unit 23 of the control unit 20 specifies the patient information image region corresponding to the outputted medical image by referring to the information table in the memory 40 using information on the display mode.

In the present embodiment, the medical image provided from the endoscope processor 10 to the recording image generating unit 70 is recorded in the recording unit 50 in a state where the patient information image remains superimposed, by the moving image file converting unit 75. At the time point of recording, mask processing on the medical image from the endoscope processor 10 is not performed, and a masked image is neither generated nor recorded.

In the present embodiment, information on the patient information image region obtained by the mask position specifying unit 23 is provided to the moving image file converting unit 75. The moving image file converting unit 75 converts the information on the patient information image region into metadata and records the metadata in the unmasked image recording region 52 of the recording unit 50 in association with the corresponding medical image. Note that the metadata is recorded every time the display mode is changed, and recorded in association with the corresponding unmasked image.

After the unmasked image and the metadata are recorded, the moving image file readout unit 76 reads out the unmasked image and the metadata recorded in the recording unit 50, and provides the unmasked image and the metadata to the image processing unit 72. The mask position setting unit 73 of the image processing unit 72 sets a region to be subjected to mask processing, that is, the patient information image region at the mask processing unit 33 on the basis of the metadata.

The mask processing unit 33 performs mask processing on the patient information image region set at the mask position setting unit 73. The mask processing unit 33 outputs the generated masked image to the moving image file converting unit 34. The moving image file converting unit 34 converts the masked image into a moving image file, provides the converted moving image file to the recording unit 50 to cause the recording unit 50 to record the converted moving image file in the masked image recording region 51 of the recording unit 50.

In this manner, in the present embodiment, only the unmasked image and the metadata of the medical image inputted from the endoscope processor are first recorded in the recording unit. After this recording, processing of generating a masked image is performed, and the masked image is recorded. In this manner, also in the present embodiment, both the medical image in which the patient information image remains superimposed and the medical image in which the patient information image is deleted are generated and recorded. In the present embodiment, because the masked image is generated and recorded after the unmasked image is generated and recorded, it is not necessary to perform processing of recording the two medical images at the same time, so that it is possible to reduce processing load upon recording of the unmasked image and recording of the masked image. Further, in the present embodiment, the masked image can be generated at an arbitrary timing. Because there is a medical image for which a masked image is not necessarily required, there may be a case where a masked image is not generated depending on setting, which makes it possible to prevent processing of generating a masked image from being uselessly performed and prevent a recording region from being uselessly consumed.

Fourth Embodiment

Figure 8:
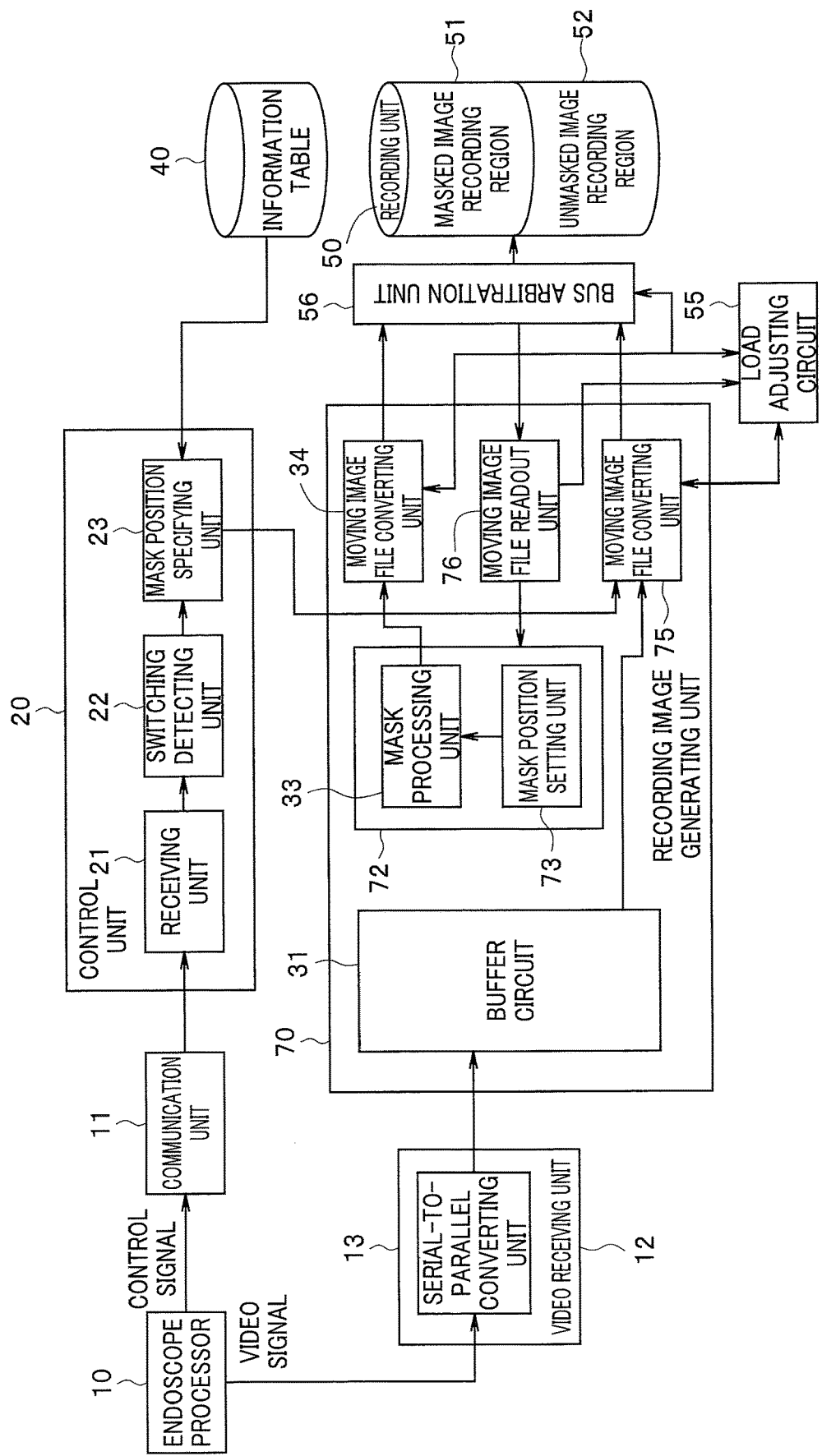
FIG. 8 is a block diagram illustrating a fourth embodiment of the present invention.

FIG. 8 is a block diagram illustrating a fourth embodiment of the present invention. In FIG. 8, the same reference numerals are assigned to components which are the same as the components in FIG. 6 and FIG. 7, and description will be omitted.

The present embodiment is combination of the second and the third embodiments, and a masked image is generated after an unmasked image is recorded, and a moving image file and metadata are transferred using one system of a communication path between the moving image file converting units 34, 75 and the moving image file readout unit 76, and the recording unit 50.

The present embodiment is different from the third embodiment in that the load adjusting circuit 55 and the bus arbitration unit 56 are added. The moving image file converting units 34, 75 provide the generated moving image files and metadata to the recording unit 50 via the bus arbitration unit 56, and the moving image file readout unit 76 reads out the moving image files and the metadata from the recording unit 50 via the bus arbitration unit 56. To the load adjusting circuit 55, information relating to data amounts of the moving image files and the metadata transmitted from the moving image file converting units 34, 75 and the moving image file readout unit 76 to the recording unit 50 is provided.

The bus arbitration unit 56 provides the moving image files and the metadata from the moving image file converting units 34, 75 to the recording unit 50, and provides the moving image file and the metadata read out from the recording unit 50 to the moving image file readout unit 76. In this case, the bus arbitration unit 56 arbitrates transmission of the moving image file from the moving image file converting unit 34, transmission of the moving image file and the metadata from the moving image file converting unit 75, and transmission of the moving image file and the metadata by the moving image file readout unit 76 by being controlled by the load adjusting circuit 55, and transmits the moving image files and the metadata in a time-division manner.

The load adjusting circuit 55 controls arbitration of the bus arbitration unit 56 on the basis of data amounts of the moving image files and the metadata outputted from the moving image file converting units 34, 75 and a data amount of the moving image file and the metadata to be read out by the moving image file readout unit 76. By this means, the bus arbitration unit 56 can reliably record the moving image files and the metadata from the moving image file converting units 34, 75 in a recording unit 50 and can reliably transfer the moving image file and the metadata from the recording unit 50 to the moving image file readout unit 76.

Note that the load adjusting circuit 55 may control the bus arbitration unit 56 so that an unmasked image from the moving image file converting unit 75 among the moving image files and the metadata to be transferred by the moving image file converting units 34, 75 and the moving image file readout unit 76 is preferentially transmitted to the recording unit 50.

In the embodiment configured in this manner, the moving image file and the metadata of the unmasked image which is a medical image in a state where the patient information image is superimposed are outputted by the moving image file converting unit 75. The moving image file and the metadata are provided to the recording unit 50 via the bus arbitration unit 56 and recorded in the unmasked image recording region 52. After the recording, the moving image file readout unit 76 reads out the unmasked image and the metadata corresponding to the unmasked image recorded in the recording unit 50 and supplies the unmasked image and the metadata to the image processing unit 72. The mask processing unit 33 of the image processing unit 72 performs mask processing on the patient information image region in the medical image to generate a masked image. The masked image is converted into a moving image file by the moving image file converting unit 34, provided to the recording unit 50 via the bus arbitration unit 56 and recorded in the masked image recording region 51.

There is a case where readout from the recording unit 50 by the moving image file readout unit 76 and writing to the recording unit 50 by the moving image file converting unit 34 occur in the same time slot. Further, there is also a possibility that upon writing to the recording unit 50 from the moving image file converting unit 75, another medical image is read out from the moving image file readout unit 76.

The load adjusting circuit 55 acquires information relating to data amounts of the moving image files and the metadata outputted by the moving image file converting units 34, 75 and a data amount of the moving image file and the metadata to be read out by the moving image file readout unit 76. The load adjusting circuit 55 controls transmission of the moving image files and the metadata generated by the moving image file converting units 34, 75 and transmission of the moving image file and the metadata to be read out by the moving image file readout unit 76 on the basis of the acquired data amounts.

The bus arbitration unit 56 reliably performs recording of the moving image files and the metadata in the recording unit 50 and readout from the recording unit 50 by controlling transmission of each piece of data in accordance with the data amounts of data transmitted by the moving image file converting units 34, 75 and the moving image file readout unit 76 by being controlled by the load adjusting circuit 55. Note that, in this case, writing of the moving image file from the moving image file converting unit 75 may be executed in preference to writing of the moving image file from the moving image file converting unit 34 and readout by the moving image file readout unit 76.

In this manner, in the present embodiment, it is possible to obtain effects similar to the effects in the second and the third embodiments.

Fifth Embodiment

Figure 9:
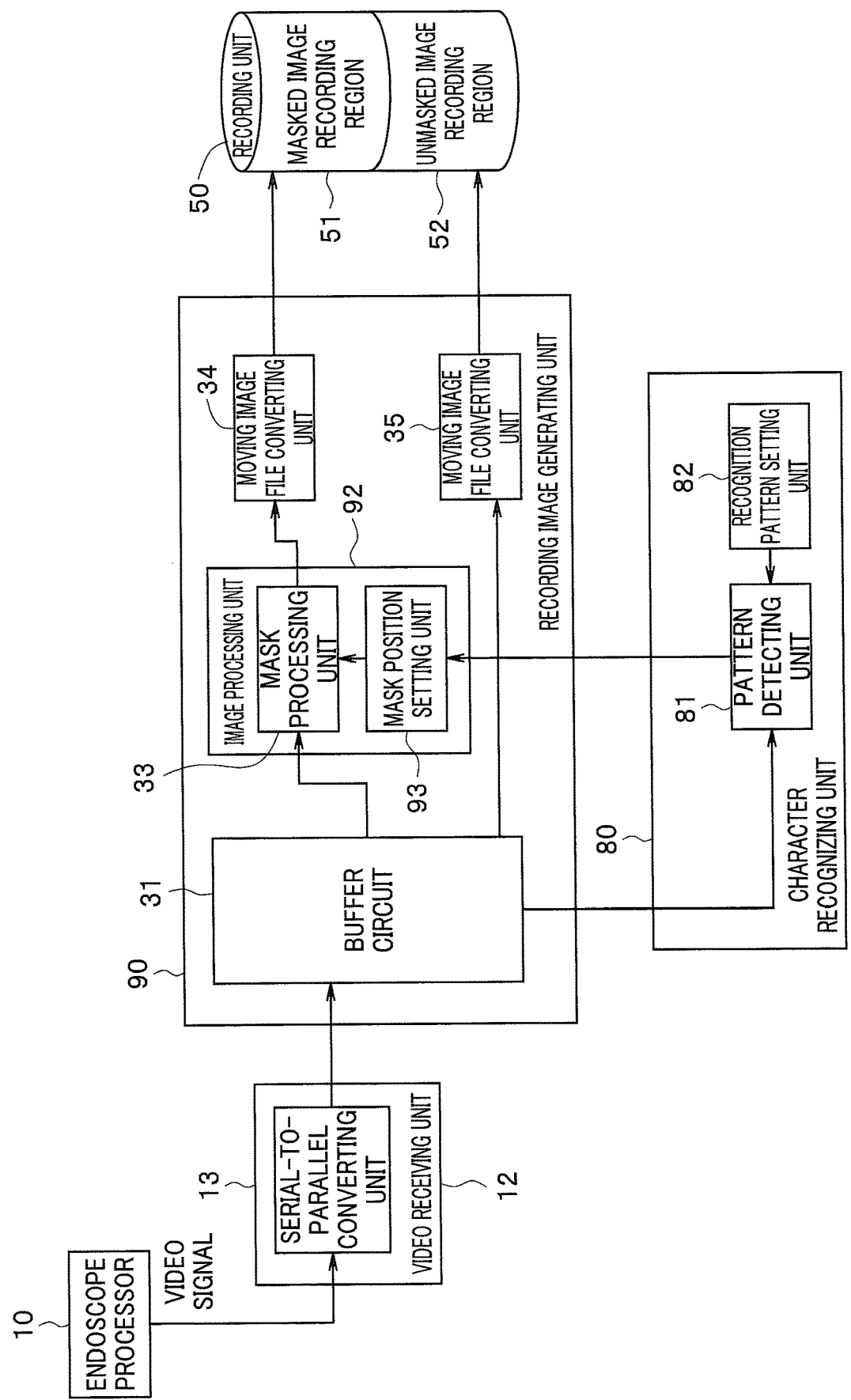
FIG. 9 is a block diagram illustrating a fifth embodiment of the present invention.

FIG. 9 is a block diagram illustrating a fifth embodiment of the present invention. In FIG. 9, the same reference numerals are assigned to components which are the same as the components in FIG. 1, and description will be omitted.

In each of the above-described embodiments, it is possible to perform mask processing on the patient information image by specifying the patient information image region on the basis of the display mode. In contrast, in the present embodiment, the patient information image region is specified through image analysis without using information on the display mode.

The embodiment in FIG. 9 is different from the embodiment in FIG. 1 in that the communication unit 11, the control unit 20 and the memory 40 in FIG. 1 are omitted, a character recognizing unit 80 is added, and a recording image generating unit 90 is employed in place of the recording image generating unit 30. The recording image generating unit 90 is different from the recording image generating unit 30 in FIG. 1 in that an image processing unit 92 is employed in place of the image processing unit 32. The image processing unit 92 includes a mask processing unit 33 and a mask position setting unit 93. The mask position setting unit 93 can set the patient information image region at the mask processing unit 33 on the basis of the information on the patient information image region from a pattern detecting unit 81 which will be described later.

A medical image is inputted to the character recognizing unit 80 from the buffer circuit 31. A recognition pattern setting unit 82 of the character recognizing unit 80 includes a memory which is not illustrated and holds information on a recognition pattern for recognizing the patient information image. For example, examples of the recognition pattern of the patient information image can include a specific character pattern, a specific marker, specific color, or the like. For example, examples of a character string indicating a patient ID included in the patient information can include "Patient No.", or the like. Further, there is also a case where a specific marker such as a filled circle and square is disposed before the character string indicating the patient information. Still further, there is also a case where a region except a character image portion in the patient information image region is filled with specific color. The recognition pattern setting unit 82 can set the recognition pattern such as the specific character pattern, the specific marker and the specific color in accordance with setting operation by the user.

The medical image from the buffer circuit 31 is provided to a pattern detecting unit 81 of the character recognizing unit 80. The pattern detecting unit 81 performs image analysis on the inputted medical image and detects a patient information image region in the medical image through comparison with the recognition pattern set by the recognition pattern setting unit 82. The pattern detecting unit 81 outputs information on the detected patient information image region to the mask position setting unit 93. In this manner, the mask position setting unit 93 can set the patient information image region at the mask processing unit 33.

Operation of the embodiment configured in this manner will be described next. The present embodiment is similar to the first embodiment in that the endoscope image from the endoscope processor 10 is supplied to the recording image generating unit 90 via the video receiving unit 12. In the present embodiment, a control signal including the information on the display mode is not outputted from the endoscope processor 10.

The buffer circuit 31 outputs the medical image to the image processing unit 92 and the moving image file converting unit 35 and also outputs the medical image to the character recognizing unit 80. The pattern detecting unit 81 of the character recognizing unit 80 performs image analysis processing on the inputted medical image, detects whether or not the recognition pattern of the recognition pattern setting unit 82 is included in the medical image, and, in the case where the recognition pattern is included, detects a region on the image including the recognition pattern as the patient information image region. The pattern detecting unit 81 outputs the information on the patient information image region to the mask position setting unit 93.

The mask position setting unit 93 sets the patient information image region obtained through image analysis at the mask processing unit 33. The mask processing unit 33 performs mask processing on the patient information image region. The mask processing unit 33 outputs the generated masked image to the moving image file converting unit 34. The moving image file converting unit 34 converts the masked image into the moving image file, and provides the converted moving image file to the recording unit 50 to cause the recording unit 50 to record the converted moving image file in the masked image recording region 51 of the recording unit 50.

In this manner, also in the present embodiment, effects similar to the effects in the first embodiment can be obtained. Further, the present embodiment has an advantage that, because the patient information image region is obtained through image analysis on the medical image inputted by the endoscope processor, it is not necessary to capture information on the display mode, and it is possible to support any display mode.

Further, while an example where the present embodiment is applied to the embodiment in FIG. 1 has been described, the present embodiment can be applied to the embodiments in FIG. 6 and FIG. 7.

Another Example

Figure 10:
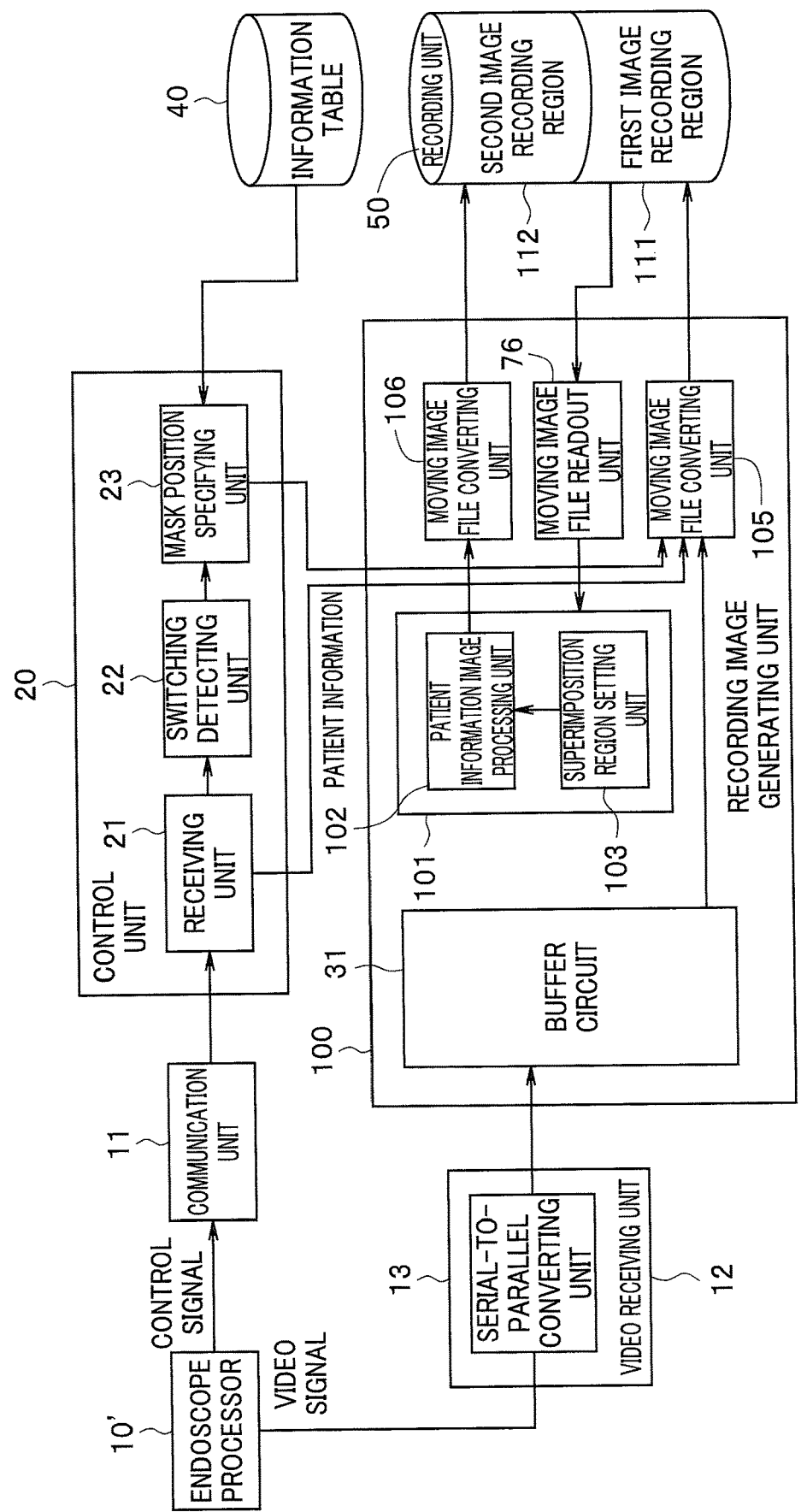
FIG. 10 is a block diagram illustrating another example.

FIG. 10 is a block diagram illustrating another example. In FIG. 10, the same reference numerals are assigned to components which are the same as the components in FIG. 7, and description will be omitted.

In each of the above-described embodiments, description has been provided assuming that the video signal of the medical image in which the patient information image is superimposed is outputted from the endoscope processor 10. In contrast, in the example in FIG. 10, a video signal of a medical image in which a patient information image from an endoscope processor 10' is not superimposed is outputted. Note that it is assumed that a control signal including information on a display mode is outputted from the endoscope processor 10'. Further, it is assumed that patient information is included in the control signal.

The example in FIG. 10 is different from the embodiment in FIG. 7 in that a recording image generating unit 100 is employed in place of the recording image generating unit 70. The recording image generating unit 100 is different from the recording image generating unit 70 in FIG. 7 in that an image processing unit 101 and moving image file converting units 106, 105 are employed respectively in place of the image processing unit 72 and the moving image file converting units 34, 75.

The mask position specifying unit 23 of the control unit 20 outputs information on the patient information image region to the moving image file converting unit 105, and, to the moving image file converting unit 105, a medical image in which the patient information image is not superimposed is provided from the buffer circuit 31, the patient information is provided from the receiving unit 21, and information on the patient information image region is provided from the mask position specifying unit 23. The moving image file converting unit 105 converts the medical image from the buffer circuit 31 into a moving image file and converts the information on the patient information image region from the mask position specifying unit 23 into metadata. The moving image file converting unit 105 records the generated moving image file and metadata, and the patient information in association with a first image recording region 111 of the recording unit 50.

The moving image file readout unit 76 can read out a medical image and metadata and patient information corresponding to the medical image recorded in the recording unit 50. The moving image file readout unit 76 outputs the read out medical image, metadata and patient information to the image processing unit 101.

The image processing unit 101 includes a patient information image processing unit 102 and a superimposition region setting unit 103. The superimposition region setting unit 103 can set the patient information image region at the patient information image processing unit 102 on the basis of the metadata from the moving image file readout unit 76. The patient information image processing unit 102 performs processing of superimposing the patient information image on the medical image read out by the moving image file readout unit 76. That is, the patient information image processing unit 102 performs superimposition processing of superimposing, for example, an image based on the patient information on the patient information image region in the read out medical image. The patient information image processing unit 102 outputs the medical image after superimposition processing to the moving image file converting unit 106. The moving image file converting unit 106 converts the medical image in which the patient information image is superimposed into a moving image file, provides the converted moving image file to the recording unit 50 and causes the recording unit 50 to record the converted moving image file in a second image recording region 112.

Operation in the example in FIG. 10 configured in this manner will be described next.

The example in FIG. 10 is similar to the first embodiment in that the endoscope image from the endoscope processor 10' is supplied to the recording image generating unit 90 via the video receiving unit 12. In the example in FIG. 10, the patient information image is not superimposed on the endoscope image from the endoscope processor 10'. Further, the control signal including the information on the display mode from the endoscope processor 10' also includes the patient information.

The receiving unit 21 extracts the patient information from the control signal and outputs the patient information to the moving image file converting unit 105 of the recording image generating unit 100. Further, the mask position specifying unit 23 acquires the information on the patient information image region based on the display data and outputs the information to the moving image file converting unit 105. The buffer circuit 31 outputs a medical image in which the patient information image is not superimposed to the moving image file converting unit 105.

The moving image file converting unit 105 converts the medical image in which the patient information image is not superimposed into a moving image file and converts the information on the patient information image region into metadata. The moving image file converting unit 105 provides the moving image file, the metadata and patient information to the recording unit 50 and causes the recording unit 50 to record the moving image file, the metadata and the patient information in the first image recording region 111.

The moving image file readout unit 76 reads out the moving image file of the medical image, the metadata and the patient information recorded in the first image recording region 111 and outputs the moving image file, the metadata and the patient information to the image processing unit 101. A superimposition region setting unit 103 of the image processing unit 101 sets the patient information image region at the patient information image processing unit 102 on the basis of the metadata from the moving image file readout unit 76. The patient information image processing unit 102 performs superimposition processing of superimposing, for example, an image based on the patient information on the patient information image region in the medical image read out by the moving image file readout unit 76. The patient information image processing unit 102 outputs the medical image in which the patient information image is superimposed through the superimposition processing to the moving image file converting unit 106. The moving image file converting unit 106 converts the medical image in which the patient information image is superimposed into a moving image file, provides the converted moving image file to the recording unit 50 and causes the recording unit 50 to record the converted moving image file in a second image recording region 112.

In this manner, also in the example in FIG. 10, it is possible to obtain medical images of both the medical image in which the patient information is superimposed and the medical image in which the patient information is not superimposed.

In this manner, also in the example in FIG. 10, it is possible to obtain effects similar to the effects in the embodiment in FIG. 7.

(Modification)

Figure 11:
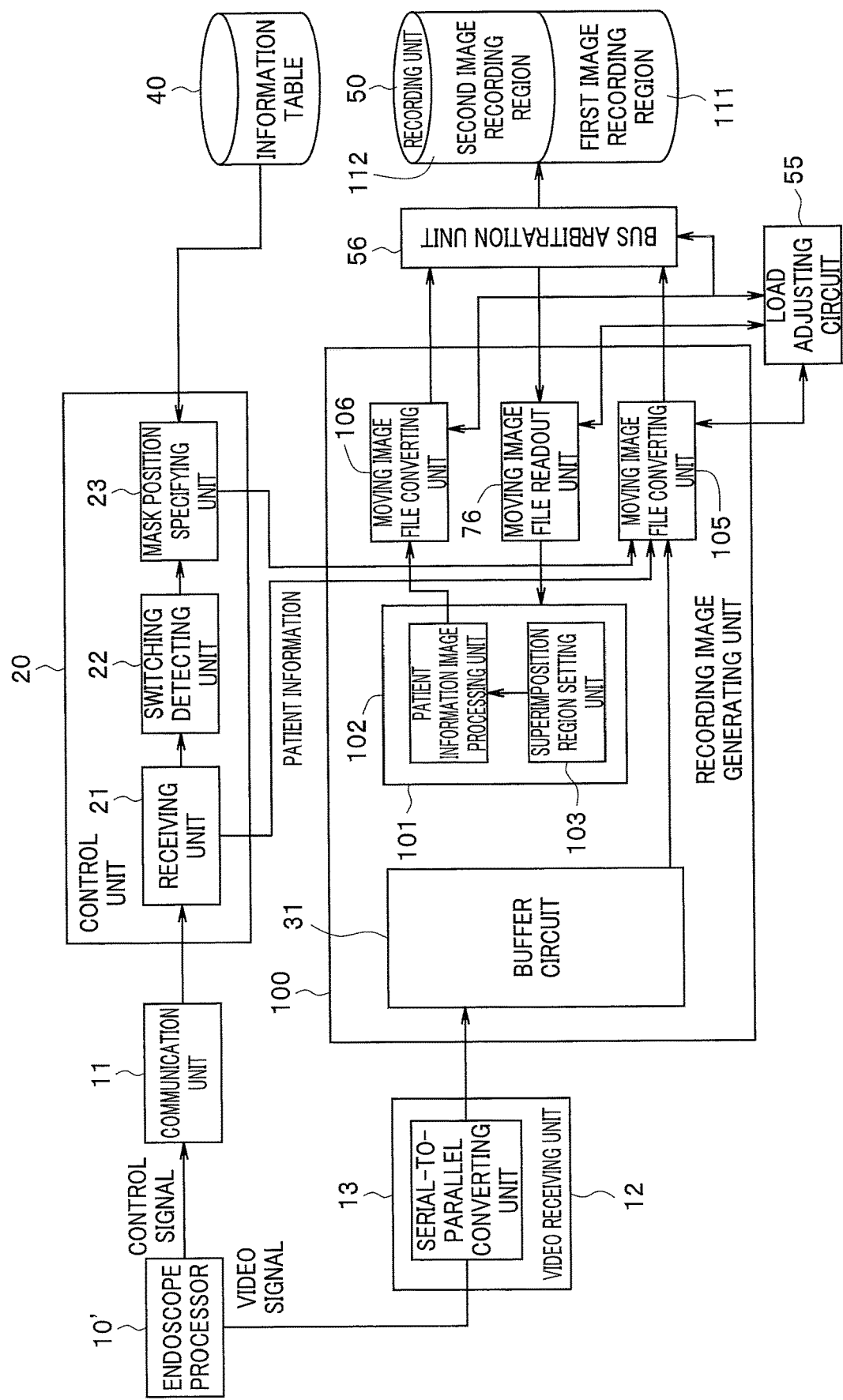
FIG. 11 is a block diagram illustrating a modification of the example in FIG. 10.

FIG. 11 is a block diagram illustrating a modification of the example in FIG. 10. In FIG. 11, the same reference numerals are assigned to components which are the same as the components in FIG. 8 and FIG. 10, and description will be omitted. The example in FIG. 11 is combination of the example in FIG. 10 and the embodiment in FIG. 8, and the moving image files, the metadata and the patient information are efficiently transmitted using one system of a communication path between the moving image file converting units 106, 105 and the moving image file readout unit 76, and the recording unit 50.

The modification in FIG. 11 is different from the example in FIG. 10 in that the load adjusting circuit 55 and the bus arbitration unit 56 are added. The moving image file converting units 105, 106 provide the generated moving image files, the metadata and the patient information to the recording unit 50 via the bus arbitration unit 56, and the moving image file readout unit 76 reads out the moving image files, the metadata and the patient information from the recording unit 50 via the bus arbitration unit 56. To the load adjusting circuit 55, information relating to data amounts of the moving image files and the metadata transmitted from the moving image file converting units 105, 106 and the moving image file readout unit 76 to the recording unit 50 is provided.

The bus arbitration unit 56 provides the moving image files, the metadata and the patient information from the moving image file converting units 105, 106 to the recording unit 50, and provides the moving image files, the metadata and the patient information read out from the recording unit 50 to the moving image file readout unit 76. In this case, the bus arbitration unit 56 arbitrates transmission of the moving image file from the moving image file converting unit 106, transmission of the moving image file, the metadata and the patient information from the moving image file converting unit 105, and transmission of the moving image file, the metadata and the patient information by the moving image file readout unit 76 by being controlled by the load adjusting circuit 55 and transmits the moving image files, the metadata and the patient information in a time-division manner.

The load adjusting circuit 55 controls arbitration by the bus arbitration unit 56 on the basis of data amounts of the moving image files, the metadata and the patient information outputted from the moving image file converting units 105, 106 and a data amount of the moving image files, the metadata and the patient information to be read out by the moving image file readout unit 76. By this means, the bus arbitration unit 56 can reliably record the moving image files, the metadata and the patient information from the moving image file converting units 105, 106 in the recording unit 50, and can reliably transfer the moving image files, the metadata and the patient information from the recording unit 50 to the moving image file readout unit 76.

Note that the load adjusting circuit 55 may control the bus arbitration unit 56 so that the unmasked image from the moving image file converting unit 75 among the moving image files, the metadata and the patient information to be transferred by the moving image file converting units 105, 106 and the moving image file readout unit 76, is preferentially transmitted to the recording unit 50.

In the modification configured in this manner, the load adjusting circuit 55 acquires information relating to data amounts of the moving image files, the metadata and the patient information outputted by the moving image file converting units 105, 106, and a data amount of the moving image file, the metadata and the patient information to be read out by the moving image file readout unit 76. The load adjusting circuit 55 controls transmission of the moving image files, the metadata and the patient information generated by the moving image file converting units 105, 106 and transmission of the moving image file, the metadata and the patient information to be read out by the moving image file readout unit 76 on the basis of the acquired data amounts.

The bus arbitration unit 56 reliably performs recording of the moving image files, the metadata and the patient information in the recording unit 50 and readout from the recording unit 50 by controlling transmission of each piece of data in accordance with the data amounts of the data to be transmitted by the moving image file converting units 105, 106 and the moving image file readout unit 76 by being controlled by the load adjusting circuit 55.

In this manner, in the present modification, it is possible to obtain effects similar to the effects in the example in FIG. 10 and the fourth embodiment.

The present invention is not limited to the above-described embodiments, and can be embodied by modifying components within a range not deviating from the gist in an implementation stage. Further, various inventions can be made by appropriate combination of a plurality of components disclosed in the above-described embodiments. For example, some of the components among all the components indicated in the embodiments may be deleted.

What is claimed is:

1. A medical information recording device comprising:
 a first recording processor configured to record a moving image of a medical image in which a status information image is superimposed;
 a second recording processor configured to record a moving image of the medical image in which a portion of the status information image in the medical image is subjected to mask processing;
 an arbitration processor configured to control communication between a memory in which the medical image in which the status information image is superimposed and the medical image in which the portion of the status information image is subjected to mask processing are recorded, and the first recording processor and the second recording processor; and
 a load adjusting circuit configured to control the arbitration processor based on a load of the first recording processor and the second recording processor.

2. The medical information recording device according to claim 1, further comprising:
 a region judging processor configured to judge a region of the status information image on the medical image for the medical image in which the status information image is superimposed; and
 a mask processing processor configured to perform mask processing on the portion of the status information image of the medical image based on a judgment result of the region judging processor, and
 wherein the load is an information amount of a moving image file.

3. The medical information recording device according to claim 1, wherein recording of the moving image by the first recording processing processor and recording of the moving image by the second recording processing processor are performed at the same time.

4. The medical information recording device according to claim 1, wherein recording of the moving image by the second recording processing processor is performed after recording of the moving image by the first recording processing processor.

5. The medical information recording device according to claim 2, wherein:
 recording of the moving image by the second recording processing processor is performed after recording of the moving image by the first recording processing processor,
 the first recording processing processor records the judgment result of the region judging processor as metadata in association with the medical image,
 the mask processing processor reads the metadata and performs the mask processing after recording of the moving image by the first recording processing processor, and
 the second recording processing processor records the moving image of the medical image in which the portion of the status information image is subjected to mask processing by the mask processing processor after recording of the moving image by the first recording processing processor.

6. The medical information recording device according to claim 2, wherein information on a display mode of the medical image in which the status information image is superimposed is provided to the region judging processor, and the region judging processor obtains a region of the status information image on the medical image based on the display mode.

7. The medical information recording device according to claim 6, wherein the region judging processor obtains the region of the status information image on the medical image every time the display mode is switched.

8. The medical information recording device according to claim 2, wherein:
recording of the moving image by the second recording processing processor is performed after recording of the moving image by the first recording processing processor,
information on a display mode of the medical image in which the status information image is superimposed is provided to the region judging processor, and the region judging processor obtains a region of the status information image on the medical image based on the display mode every time the display mode is switched,
the first recording processing processor records the judgement result of the region judging processor as metadata in association with the medical image every time the display mode is switched,
the mask processing processor reads the metadata and performs the mask processing after recording of the moving image by the first recording processing processor, and
the second recording processing processor records a moving image of the medical image in which the portion of the status information image is subjected to mask processing by the mask processing processor after recording of the moving image by the first recording processing processor.

9. The medical information recording device according to claim 2, wherein the medical image in which the status information image is superimposed is provided to the region judging processor, and the region judging processor obtains a region of the status information image on the medical image through image analysis of the medical image.

10. The medical information recording device according to claim 2, wherein the mask processing processor performs mask processing through filling processing with respect to the portion of the status information image or mosaic processing with respect to the portion of the status information image.

11. A medical information recording device comprising:
a region judging processor configured to, for a medical image in which a status information image is superimposed, (i) obtain a region of the status information image on the medical image through image analysis of the medical image, and (ii) determine the region of the status information image;
a first recording processor configured to record a moving image of the medical image in which the status information image is superimposed;
a mask processor configured to mask a portion of the status information image of the medical image based on determining the region of the status information image; and
a second recording processing processor configured to record a moving image of the medical image in which the portion of the status information image is subjected to mask processing by the mask processing processor.

12. The medical information recording device according to claim 1, wherein the status information image is a patient information image.

13. The medical information recording device according to claim 2, wherein region judging processor is configured to:
perform image analysis on the medical image in which the status information image is superimposed, and
determine the region of the status information image through character recognition processing by pattern detection.

14. A medical information recording method comprising:
recording in a first memory region, using a first recording processor, a moving image of a medical image in which a status information image is superimposed;
recording in a second memory region, using a second recording processor, a moving image of the medical image in which a portion of the status information image in the medical image is subjected to mask processing;
controlling, using an arbitration processor, communication between a memory in which the medical image in which the status information image is superimposed and the medical image in which the portion of the status information image is subjected to mask processing are recorded, and the first recording processor and the second recording processor; and
controlling, using a load adjusting circuit, the arbitration processor based on a load of the first recording processor and the second recording processor.

* * * * *